(12) United States Patent
Fendler

(10) Patent No.: US 9,463,297 B2
(45) Date of Patent: Oct. 11, 2016

(54) APPARATUS FOR ASPIRATING THE SPUTUM IN TRACHEOTOMY PATIENTS AND INNER CANNULA FOR A TRACHEAL CANNULA

(75) Inventor: Helmut Fendler, Nuremberg (DE)

(73) Assignee: Gesundheitsmanager GmbH, Schwaig (DE)

( * ) Notice: Subject to any disclaimer, the term of this patent is extended or adjusted under 35 U.S.C. 154(b) by 64 days.

(21) Appl. No.: 13/509,745

(22) PCT Filed: Nov. 4, 2010

(86) PCT No.: PCT/EP2010/006711
§ 371 (c)(1),
(2), (4) Date: May 14, 2012

(87) PCT Pub. No.: WO2011/054507
PCT Pub. Date: May 12, 2011

(65) Prior Publication Data
US 2012/0247473 A1     Oct. 4, 2012

(30) Foreign Application Priority Data
Nov. 6, 2009 (DE) .................... 20 2009 015 123 U

(51) Int. Cl.
| A61M 1/00 | (2006.01) |
| A61M 16/04 | (2006.01) |
| A61M 27/00 | (2006.01) |
| A61M 16/00 | (2006.01) |

(52) U.S. Cl.
CPC ..... *A61M 16/0465* (2013.01); *A61M 16/0463* (2013.01); *A61M 16/0479* (2014.02); *A61M 16/04* (2013.01); *A61M 16/0434* (2013.01)

(58) Field of Classification Search
CPC ........... A61M 16/04; A61M 16/0434; A61M 16/0479; A61M 16/0465; A61M 16/0463
USPC ........................ 604/317, 319, 326, 327, 541; 128/207.14, 207.16, 207.29
See application file for complete search history.

(56) References Cited

U.S. PATENT DOCUMENTS

| 3,087,493 A | * | 4/1963 | Schossow ................. 128/207.15 |
| 3,262,318 A | * | 7/1966 | Decker .................... G01N 1/08 |
| | | | 406/152 |
| 4,502,482 A | * | 3/1985 | DeLuccia et al. ....... 128/207.15 |

(Continued)

FOREIGN PATENT DOCUMENTS

| DE | 101 09 935 A1 | 11/2001 |
| WO | 03/101516 A1 | 12/2003 |
| WO | 2007/130579 A2 | 11/2007 |

*Primary Examiner* — Tatyana Zalukaeva
*Assistant Examiner* — Andrew J Mensh
(74) *Attorney, Agent, or Firm* — Laurence A. Greenberg; Werner H. Stemer; Ralph E. Locher

(57) ABSTRACT

In order to make automatic suctioning of sputum in tracheotomy patients possible, the suctioning device includes a tracheal cannula having an external cannula and an internal cannula guided therein. The internal cannula is formed with suction openings for internal suctioning and is spaced apart from the external cannula to form a suction chamber. The suction chamber is connected to a suction connection, by way of which a suction apparatus can be connected. As an alternative, or in addition, the external cannula has additional suction openings for external suction in the region of a cuff. In this way, automated suctioning of sputum in patients, in particular in a gentle manner, is made possible.

15 Claims, 1 Drawing Sheet

(56) References Cited

U.S. PATENT DOCUMENTS

| | | | | |
|---|---|---|---|---|
| 4,632,108 A | * | 12/1986 | Geil | 128/207.14 |
| 4,637,389 A | * | 1/1987 | Heyden | 128/207.15 |
| 5,056,515 A | * | 10/1991 | Abel | 128/207.15 |
| 5,073,164 A | * | 12/1991 | Hollister et al. | 604/43 |
| 5,360,414 A | * | 11/1994 | Yarger | 604/264 |
| 5,470,308 A | * | 11/1995 | Edwards et al. | 604/22 |
| 5,515,844 A | * | 5/1996 | Christopher | A61M 16/10 128/200.26 |
| 5,582,167 A | * | 12/1996 | Joseph | 128/207.15 |
| 6,725,862 B2 | * | 4/2004 | Klinberg et al. | 128/207.14 |
| 7,258,120 B2 | * | 8/2007 | Melker | 128/207.14 |
| RE41,345 E | * | 5/2010 | Blom | 128/207.14 |
| 2002/0014238 A1 | * | 2/2002 | Kotmel | A61M 16/04 128/204.18 |
| 2004/0079376 A1 | | 4/2004 | Melker | |
| 2008/0011304 A1 | | 1/2008 | Stewart | |

* cited by examiner

APPARATUS FOR ASPIRATING THE SPUTUM IN TRACHEOTOMY PATIENTS AND INNER CANNULA FOR A TRACHEAL CANNULA

BACKGROUND OF THE INVENTION

Field of the Invention

The invention relates to an apparatus for aspirating the sputum in tracheotomy patients, comprising a tracheal cannula which has an outer cannula and an inner cannula guided in the latter. The invention also relates to an inner cannula of this kind.

A tracheal cannula of this kind can be found for example in DE 10 2006 035 887 A1.

In tracheotomy patients, access to the windpipe is created from the outside in the neck area with the aid of a cannula, known as a breathing cannula or tracheal cannula. Cannulas of this kind are used for example in patients in a persistent vegetative state after accidents or operations. In order to ensure reliable functioning, the interior of the cannula has to be aspirated regularly on account of the formation of mucous, what are known as secretions or sputum.

Cannulas of this kind are sometimes provided with an inflatable balloon, known as the "cuff", which is arranged around the outer circumference of the cannula and seals off the cannula within the windpipe from the wall of the windpipe. This is intended to prevent pharyngeal secretions/sputum and foreign bodies (e.g. food remnants) from passing into the lungs and causing inflammations there. The pharyngeal secretions accumulating at the top side of the cuff likewise have to be aspirated regularly.

BRIEF SUMMARY OF THE INVENTION

It is the object of the invention to ensure aspiration of secretions in tracheotomy patients which is as gentle and reliable as possible.

The object is achieved according to the invention by an apparatus having the features as claimed. Accordingly, there is provided a tracheal cannula which has an outer cannula and an inner cannula guided in the latter. The inner cannula is arranged in a manner spaced apart from the outer cannula in order to form a suction space. Furthermore, there is provided a suction connection which is connected to this suction space and to which an aspiration device is connected in operation. Depending on the configuration of the tracheal cannula, internal aspiration, external aspiration or combined internal and external aspiration is made possible via the suction space. For internal aspiration, the inner cannula is provided with suction openings. For external aspiration, the outer cannula is provided with further suction openings in the region above a cuff. In the combined configuration, both the suction openings in the inner cannula and the further suction openings in the outer cannula are provided.

This configuration achieves the decisive advantage that between the two cannulas there is formed a usually annular suction space, via which—when a corresponding negative pressure is applied via the aspiration device—a draw, that is to say a suction action, is achieved, such that a negative pressure is produced by comparison in the suction space, and so sputum is drawn into the suction space and is aspirated from there by means of the aspiration device.

In the case of internal aspiration, sputum is drawn via the suction openings from the interior of the inner cannula into the suction space in the manner of slurping suction.

For external aspiration, the tracheal cannula has the "cuff" on the outer cannula, wherein pharyngeal secretions which accumulate above the cuff are drawn into the suction space from outside via the further suction openings.

For this purpose, there is no need for manual intervention, which is a strain on the patient. Also, during aspiration, the functioning of the tracheal cannula is not impaired. Overall, therefore, this measure allows removal of the sputum in a manner which is gentle to the patient and at the same time safe, thereby increasing the well-being of the patient, and—in the case of internal aspiration—ensuring continuous aeration of the lungs.

The size of the suction openings and also of the further suction openings is selected such that said suction openings ensure reliable aspiration of the sputum. For the functional reliability of the cannula, the development of the negative pressure in the suction space and the development of a corresponding draw via the suction openings is of considerable importance. Therefore, in particular for the internal aspiration, the cannula is designed such that the production of the negative pressure in the suction space is ensured by way of the drawing action toward the interior of the inner cannula. To this end, it is in particular provided that the outer cannula is closed in the region of the suction openings for internal aspiration and itself has no openings.

With regard to aspiration which is as efficient as possible, the suction openings are arranged in a manner distributed preferably along the entire length of the inner cannula, in particular at least along a majority of the length (>50%, in particular >75% of the length). The individual suction openings thus form a kind of perforation of the inner cannula along at least a majority of the length thereof, preferably along the entire length. Perforation is understood here to mean a multiplicity of regularly or irregularly distributed openings having a sufficient diameter for aspirating the sputum.

For aspiration which is as regular as possible, in a preferred development, an encircling arrangement of the individual suction openings around the entire circumference of the inner cannula is provided. In this case, said suction openings are arranged for example in a manner distributed regularly around the circumference.

In a preferred refinement, the suction openings have a size that varies in the longitudinal direction, and in particular the size decreases in this case toward the distal end. The larger suction openings are therefore located at the proximal end, such that the greatest suction action is achieved there at the lower end of the tracheal cannula.

The further suction openings for external aspiration are arranged preferably exclusively directly adjacent to the cuff.

Thus, while the suction openings in the inner cannula for internal aspiration extend along a long length region and preferably along the entire length of the inner cannula, the further suction openings for external aspiration are formed merely in a tightly delimited region directly adjacent to the cuff. By way of these further suction openings, the particular advantage is achieved that both internal aspiration and external aspiration takes place in parallel in a reliable manner which is gentle to patients via only one common suction space and one aspiration device. Therefore, no additional aspiration measures are required for external aspiration. Therefore, in the region of the cuff, a suction action from the external region into the suction space is achieved via the further suction openings.

The further suction openings for external aspiration are in this case arranged preferably in a manner encircling the outer cannula in the manner of a ring.

Preferably, the further suction openings—as seen in the longitudinal direction of the cannula—are arranged only in a few rows, in particular merely in one or possibly two rows. This ensures that in the further region toward the distal end of the tracheal cannula, the suction power is directed exclusively toward the interior of the inner cannula, in order to ensure the functionality of the internal aspiration.

In order to form the suction space, in a preferred refinement at least one spacer is provided in order to keep the inner cannula spaced apart in a defined position from the outer cannula, in particular in a concentric arrangement.

The number and also the configuration of the spacers are selectable within wide ranges, depending also on the rigidity of the inner and outer cannulas. Thus, in a preferred variant, it is provided to arrange at the proximal end a (single), for example annular, spacer between the two cannulas. Said spacer serves, in the manner of a sealing ring, preferably at the same time to seal off the end side of the suction space in the direction of the windpipe.

Additionally, or in an alternative refinement, there are provided a plurality of spacers, which extend in the longitudinal direction and are distributed around the circumference and are preferably formed for example approximately in the form of studs. In a preferred alternative, a plurality of spacers formed as external webs are provided. These spacers extend preferably parallel to one another in the longitudinal direction of the inner cannula. They are spaced apart regularly from one another and between them there are formed in each case a multiplicity of suction openings. The spacers are in this case formed preferably on the inner cannula, such that the outer cannula—apart from the further suction openings that are possibly additionally provided in the region of the cuff—is a conventional, closed tubular cannula.

In a preferred refinement, the aspiration device is part of the apparatus and can be connected to the suction connection via a suction hose and is connected thereto in operation. The aspiration device has in particular an aspiration pump and a collecting vessel for the aspirated secretions.

In this case, in a preferred refinement, the suction connection is provided circumferentially on the outer cannula, such that radial aspiration thus takes place. Therefore, at the distal end, the outer cannula has on its circumference an aspiration opening which is formed by the suction connection and via which the secretions drawn into the suction space are aspirated in the direction of the pump.

In a preferred development, there is provided a control unit, via which automated aspiration takes place without manual intervention being necessary. Expediently, aspiration is carried out via the suction device as required, for example in definable time intervals and for a settable duration. The time intervals between the individual aspiration operations and/or the duration of a respective aspiration operation can in this case be set at the control unit preferably by the nursing staff. The control unit is integrated in particular into the aspiration device.

The object is also achieved according to the invention by an inner cannula for an apparatus of this kind.

BRIEF DESCRIPTION OF THE SEVERAL VIEWS OF THE DRAWING

An exemplary embodiment of the invention is explained in more detail in the following text on the basis of the drawings, in which.

DESCRIPTION OF THE INVENTION

Figure 1:
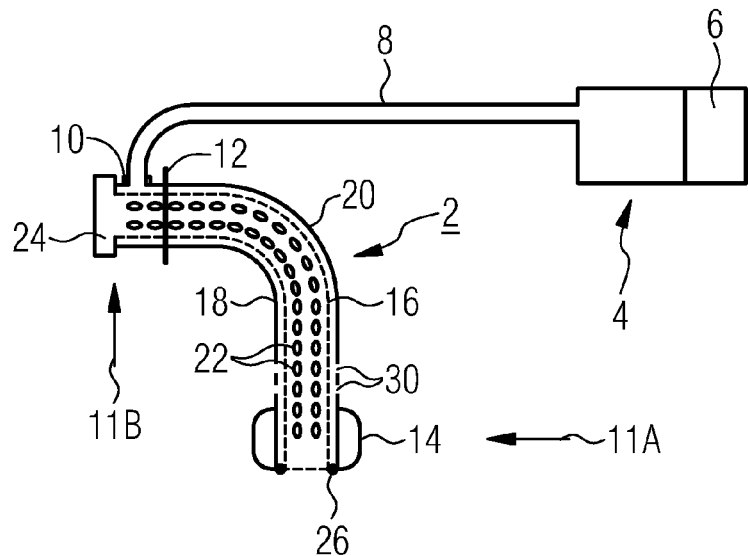
FIG. 1 shows a schematic illustration of an apparatus for aspirating the sputum in tracheotomy patients, having a tracheal cannula according to a first variant.

The apparatus illustrated in FIG. 1 comprises a tracheal cannula 2 and also an aspiration device 4 and a control unit 6, which is integrated in the aspiration device 4 in the exemplary embodiment. The aspiration device 4 comprises a pump or suction unit (not illustrated in more detail) for generating a negative pressure. In addition, a collecting vessel (likewise not shown) for the aspirated secretions is part of the aspiration device 4. In operation, the aspiration device 4 is connected via an aspiration line 8 to the tracheal cannula 2 via a suction connection 10 in the form of a connection stub. The tracheal cannula 2 extends generally from a proximal end 11A inside the body to a distal end 11B outside the body. The suction connection 10 is provided in the region between the distal end 11B and a collar 12 as a radial connection in the outer wall of the outer cannula 18 and creates a connection to the suction space 20.

The apparatus illustrated is used in tracheotomy patients. To this end, the tracheal cannula 2 is introduced from the outside into the windpipe via an incision in the neck area of the patient, with the proximal end 11A at the front. On the outside close to its distal end 11B, the tracheal cannula 2 has the collar 12, and the tracheal cannula 2 is introduced into the neck area as far as said collar 12. The tracheal cannula 2 is thus supported externally on the neck of the patient by way of the collar 12.

In tracheotomy patients, there is generally the problem that the tracheal cannula can become at least partially clogged with body secretions (sputum, mucous) and thus breathing can be made more difficult.

A further problem is that pharyngeal secretions or foreign bodies can pass along the outer side of the tracheal cannula 2 and into the lungs and can lead to inflammations there. In order to avoid this, the tracheal cannula 2 usually has at its distal end 11B an inflatable balloon, known as a cuff 14, which prevents pharyngeal secretions from being able to pass into the lungs in the intermediate space between the tracheal cannula 2 and the wall of the windpipe. The pharyngeal secretions accumulate above the cuff 14. Here, too, regular aspiration is necessary. To this end, it can for example be provided that a suction hose is guided along the outer side of the tracheal cannula 2 in the direction of the cuff 14 in order to aspirate the pharyngeal secretions that have accumulated there.

In order to aspirate the sputum as efficiently as possible from the interior of the tracheal cannula 2, the latter has a special, substantially two-part structure consisting of an inner cannula 16 and also an outer cannula 18. The inner cannula 16 is arranged in a preferably concentric manner within the outer cannula 18 with an intermediate space being left free. The intermediate space is in particular an annular gap as seen in cross section. This intermediate space forms a suction space 20. The inner cannula 16 has suction openings 22 preferably along its entire length. The suction openings 22 are in this case arranged preferably in a regularly distributed manner and have a sufficient size to allow aspiration of sputum from the interior of the inner cannula 16 into the suction space 20.

At its distal end 11B, the inner cannula 16 has a preferably conically widening encircling connection ring 24 or sealing ring, by way of which the inner cannula 16 fits in the outer cannula 18 with a precise fit and in a sealing manner. Thus, the connection ring 24 forms at the same time a kind of spacer, such that the inner cannula 16 is held concentrically in the outer cannula 18.

In the exemplary embodiment in FIG. 1, a sealing ring 26 is additionally also arranged at the proximal end 11A, said sealing ring 26 likewise acting in the manner of a spacer. Depending on the rigidity of the cannulas 16, 18, it is possible under certain circumstances to dispense with this sealing ring 26 as spacer. With regard to the suction action, it is advantageous, since as a result the suction space, together with the connection ring 24, is sealed off in each case at the proximal end 11A and distal end 11B.

Figure 2:
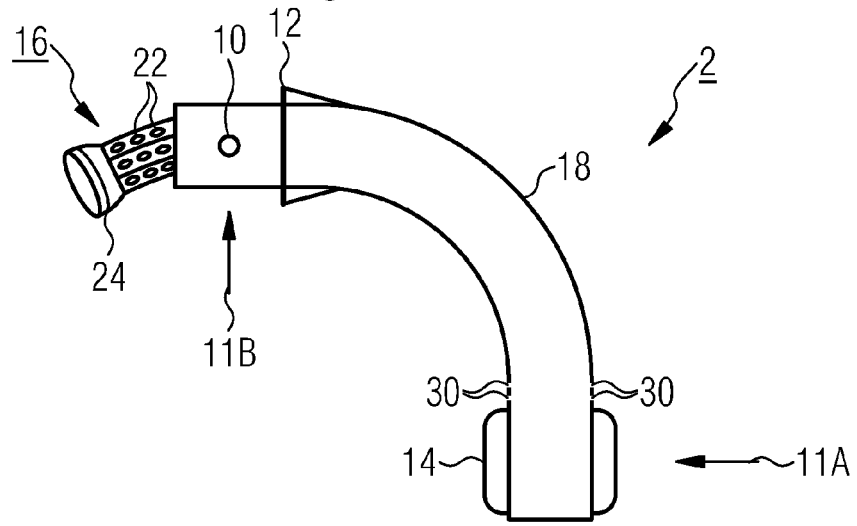
FIG. 2 shows a schematic side view of a tracheal cannula according to a second variant.
Figure 3:
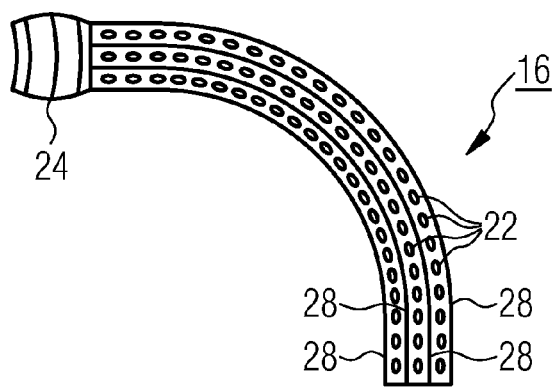
FIG. 3 shows a side view of an inner cannula of the tracheal cannula according to FIG. 2.

In an alternative refinement, as is illustrated in FIGS. 2 and 3, longitudinal webs 28 are formed as spacers on the outer side of the inner cannula 16. In the exemplary embodiment, these longitudinal webs 28 are formed directly out of the wall of the inner cannula 16, for example in the manner of a star. In the exemplary embodiment, six regularly distributed longitudinal webs 28 are provided. The suction openings 22 are in each case formed between adjacent webs.

Instead of the longitudinal webs, other spacers, such as studs or the like, for example, are also possible. As an alternative to the arrangement on the inner cannula 16, they can also be arranged on the inner wall of the outer cannula 18.

In order to aspirate the sputum, the aspiration line 8, and via the latter the aspiration apparatus 4, is connected at the suction connection 10. The aspiration apparatus 4 generates a negative pressure, such that a draw is generated from the interior of the inner cannula 16, via the suction opening 22 and into the suction space 20. On account of this drawing action, sputum located in the inner cannula 16 is therefore aspirated through the suction opening 22 into the suction space 20 and from there via the aspiration line 18 to the aspiration device 4. This special configuration of the inner cannula 16 allows automated aspiration which is in particular gentle to a patient, without breathing having to be interrupted.

Expediently, the aspiration device 4 and the control unit 6 integrated therein are designed for automated aspiration, for example continuously or else in an intermittent manner in specific time intervals.

In addition to this aspiration, known as internal aspiration, of the sputum from the interior of the inner cannula 16, aspiration, known as external aspiration, of the pharyngeal secretions accumulating above the cuff 14 is provided.

To this end, the outer cannula 18 has further suction openings 30 in the region immediately above the cuff 14. These further suction openings 30 are therefore likewise connected to the suction space 20. During operation of the aspiration device 4, the pharyngeal secretions are aspirated inwardly from the outer space into the suction space 20 via these further suction openings 30 and are aspirated from said suction space 20. The further suction openings 30 are arranged exclusively in the region close to the cuff 14 and extend for example 1 cm to 2 cm above the cuff 14. Otherwise, the outer cannula is formed in a conventional manner as a closed hose. In one configuration as what is known as a speech cannula, as is known for example from DE 10 2006 035 887 A1, windows which are assigned to one another can additionally be provided on the inner cannula 16 and on the outer cannula 18.

For the aspiration described here, it is generally of considerable importance that the suction openings 22 are provided along a length region of the inner cannula which is as long as possible and a negative pressure can develop in the suction space 20 and the suction space 20 can be connected to the aspiration device 4. The suction openings 22 extend preferably along more than 50%, in particular more than 75% of the length of the inner cannula 16. Furthermore, the suction openings 22 are arranged in a manner encircling the entire circumference of the inner cannula 16.

In a simple configuration, the outer cannula 18 is in the form of a closed tube or of a closed hose. Both cannulas 16, 18 consist of a suitable plastics material. In the combination having external aspiration, the outer cannula 18 has the further suction openings 30 only in the region above the cuff 14.

By way of the additional further suction openings 30, the particular advantage is achieved that both internal aspiration and external aspiration can take place in an automated manner which is gentle to the patient with only one aspiration device. Overall, the tracheal cannula 2 described here and having the specially designed inner cannula 16 and the design of the suction space 20 allows automated aspiration in a manner gentle to a patient.

As an alternative to the described exemplary embodiments, which show a tracheal cannula 2 both for internal aspiration and for external aspiration, in the case of purely internal aspiration, no further suction openings 30 are provided in the outer cannula 18 and the latter is formed by a closed tube. In the case of purely external aspiration, the inner cannula 16 is in the form of a closed tube and no suction openings 22 are provided.

LIST OF REFERENCE SIGNS

2 Tracheal cannula
4 Aspiration device
6 Control unit
8 Aspiration line
10 Connection stub
11A Proximal end
11B Distal end
12 Collar
14 Cuff
16 Inner cannula
18 Outer cannula
20 Suction space
22 Suction opening
24 Terminating ring
26 Sealing ring
28 Longitudinal web

The invention claimed is:

1. An apparatus for aspirating sputum in tracheotomy patients, the apparatus comprising:
a tracheal cannula including an outer cannula and an inner cannula guided in said outer cannula, said tracheal cannula extending from a distal end to a proximal end;
said inner cannula being disposed concentrically in said outer cannula and spaced apart from said outer cannula for forming a suction space therebetween, said inner cannula having an inner cannula wall and said outer cannula having an outer cannula wall;
a suction connection disposed on said outer cannula and communicating with said suction space, for connection to an aspiration device; and
said inner cannula being formed with suction openings in said inner cannula wall for internal aspiration, said suction openings being formed encircling a circumference of said inner cannula, said suction connection communicating with said suction space for generating a draw from an interior of said inner cannula via said suction openings into said suction space.

2. An apparatus for aspirating sputum in tracheotomy patients, the apparatus comprising:
   a tracheal cannula including an outer cannula and an inner cannula guided in said outer cannula, said tracheal cannula extending from a distal end to a proximal end;
   a cuff disposed on said outer cannula at said proximal end;
   said inner cannula being disposed concentrically in said outer cannula and spaced apart from said outer cannula for forming a suction space therebetween, said inner cannula having an inner cannula wall and said outer cannula having an outer cannula wall;
   a suction connection disposed on said outer cannula and communicating with said suction space, for connection to an aspiration device; and
   said inner cannula being formed with suction openings in said inner cannula wall substantially along an entire length thereof above said cuff in a direction to said distal end for internal aspiration, said suction connection communicating with said suction space for generating a draw from an interior of said inner cannula via said suction openings into said suction space.

3. The apparatus according to claim 2, wherein said suction openings are in the form of a perforation.

4. An apparatus for aspirating sputum in tracheotomy patients, the apparatus comprising:
   a tracheal cannula including an outer cannula and an inner cannula guided in said outer cannula, said tracheal cannula extending from a distal end to a proximal end;
   said inner cannula being disposed concentrically in said outer cannula and spaced apart from said outer cannula for forming a suction space therebetween, said inner cannula having an inner cannula wall and said outer cannula having an outer cannula wall;
   a suction connection disposed on said outer cannula and communicating with said suction space, for connection to an aspiration device; and
   said inner cannula being formed with suction openings in said inner cannula wall for internal aspiration, a cross-sectional area of said suction openings varying in a longitudinal direction of said inner cannula, said suction connection communicating with said suction space for generating a draw from an interior of said inner cannula via said suction openings into said suction space.

5. The apparatus according to claim 4, wherein said cross-sectional area of said suction openings decreases toward a distal end.

6. The apparatus according to claim 1, which comprises at least one spacer disposed in said annular suction space to space apart said inner cannula from said outer cannula.

7. The apparatus according to claim 6, wherein said at least one spacer is one of a plurality of spacers formed as longitudinal webs.

8. The apparatus according to claim 1, which comprises the aspiration device connected to said suction connection in operation of the apparatus.

9. The apparatus according to claim 1, wherein said suction connection is formed radially on a periphery of said outer cannula.

10. The apparatus according to claim 8, wherein said aspiration device includes a control unit configured to set automated aspiration.

11. The apparatus according to claim 10, wherein said control unit is configured to be set for automated aspiration at predefined time intervals.

12. The apparatus according to claim 1, wherein said suction space is an annular suction space.

13. An apparatus for aspirating sputum in tracheotomy patients, the apparatus comprising:
   a tracheal cannula including an outer cannula and an inner cannula guided in said outer cannula, said tracheal cannula extending from a distal end to a proximal end;
   said inner cannula being disposed concentrically in said outer cannula and spaced apart from said outer cannula for forming a suction space therebetween, said inner cannula having an inner cannula wall and said outer cannula having an outer cannula wall;
   a suction connection disposed on said outer cannula and communicating with said suction space, for connection to an aspiration device; and
   wherein one or both of the following are true:
   said inner cannula is formed with suction openings in said inner cannula wall for internal aspiration, said suction connection communicating with said suction space for generating a draw from an interior of said inner cannula via said suction openings into said suction space; and/or a cuff is disposed on said outer cannula at said proximal end and said outer cannula has further suction openings formed in said outer cannula wall, adjacent said cuff and between said cuff and said distal end, for external aspiration, and said outer cannula being closed in a region of said suction openings of said inner cannula.

14. An apparatus for aspirating sputum in tracheotomy patients, the apparatus comprising:
   a tracheal cannula including an outer cannula and an inner cannula guided in said outer cannula, said tracheal cannula extending from a distal end to a proximal end;
   said inner cannula being disposed concentrically in said outer cannula and spaced apart from said outer cannula for forming a suction space therebetween, said inner cannula having an inner cannula wall and said outer cannula having an outer cannula wall;
   a suction connection disposed on said outer cannula and communicating with said suction space, for connection to an aspiration device; and
   said inner cannula being formed with suction openings in said inner cannula wall for internal aspiration, said suction connection communicating with said suction space for generating a draw from an interior of said inner cannula via said suction openings into said suction space; and
   a cuff disposed on said outer cannula at said proximal end and said outer cannula having further suction openings formed in said outer cannula wall, adjacent said cuff and between said cuff and said distal end, for external aspiration.

15. The apparatus according to claim 14, wherein said outer cannula is closed in a region of said suction openings in said inner cannula wall.

* * * * *